(12) United States Patent
Judd

(10) Patent No.: US 11,367,974 B1
(45) Date of Patent: Jun. 21, 2022

(54) ECG ELECTRODE CONNECTOR

(71) Applicant: Daniel R. Judd, Burlington, MA (US)

(72) Inventor: Daniel R. Judd, Burlington, MA (US)

( * ) Notice: Subject to any disclaimer, the term of this patent is extended or adjusted under 35 U.S.C. 154(b) by 0 days.

(21) Appl. No.: 17/304,078

(22) Filed: Jun. 14, 2021

(51) Int. Cl.
| | | |
|---|---|---|
| *H01R 12/71* | (2011.01) | |
| *A61B 5/274* | (2021.01) | |
| *H01R 13/24* | (2006.01) | |
| *H01R 13/03* | (2006.01) | |
| *H01R 43/16* | (2006.01) | |
| *A61B 5/28* | (2021.01) | |
| *A61B 5/263* | (2021.01) | |

(52) U.S. Cl.
CPC ......... *H01R 13/2457* (2013.01); *A61B 5/263* (2021.01); *A61B 5/274* (2021.01); *A61B 5/28* (2021.01); *H01R 12/718* (2013.01); *H01R 13/03* (2013.01); *H01R 43/16* (2013.01); *A61B 2562/0215* (2017.08); *H01R 2201/12* (2013.01); *H01R 2201/20* (2013.01)

(58) Field of Classification Search
CPC .. H01R 13/2457; H01R 12/718; H01R 13/03; H01R 43/16; H01R 2201/12; H01R 2201/20; A61B 5/263; A61B 5/274; A61B 5/28; A61B 2562/0215
See application file for complete search history.

(56) References Cited

U.S. PATENT DOCUMENTS

| | | | |
|---|---|---|---|
| 4,671,591 A | 6/1987 | Archer | |
| 4,842,557 A | 6/1989 | Muz | |
| 5,037,315 A | 8/1991 | Colier et al. | |
| 5,168,876 A * | 12/1992 | Quedens | A61B 5/288 600/376 |
| 5,232,383 A | 8/1993 | Barnick | |
| 5,454,739 A | 10/1995 | Strand | |
| 6,487,430 B1 | 11/2002 | Handerson et al. | |
| 6,780,065 B2 | 8/2004 | Schwarz | |
| 7,081,026 B2 | 7/2006 | Schwarz | |
| 7,108,529 B1 | 9/2006 | Huang | |
| 7,445,522 B2 | 11/2008 | Burnes | |
| 7,833,032 B1 | 11/2010 | Yu | |
| 8,123,576 B2 | 2/2012 | Kim | |
| 9,893,438 B1 * | 2/2018 | Oster | A44B 17/0041 |
| 10,010,259 B2 | 7/2018 | Kaminski | |
| 2006/0110962 A1 * | 5/2006 | Powell | H01R 11/22 439/169 |
| 2011/0151728 A1 * | 6/2011 | Astola | H01R 11/22 439/733.1 |
| 2015/0111399 A1 * | 4/2015 | Karls | A61B 5/24 439/39 |
| 2015/0327788 A1 * | 11/2015 | Wandler | A61N 1/048 600/394 |
| 2018/0132791 A1 * | 5/2018 | Chen | A61B 5/7203 |
| 2021/0044065 A1 * | 2/2021 | Barth | H01R 13/627 |

* cited by examiner

*Primary Examiner* — Michael C Zarroli

(57) ABSTRACT

A compact ECG snap connector is disclosed. A channeled U shaped body is formed from a thin sheet of electrically conductive and resilient material. The body is dimensioned to be compatible with standard ECG snap connector pins, and can be fastened to a printed circuit board. Fixed structures located in proximity to the channeled U shaped body provide mechanical restrictions on the expansion and contraction of the channeled U shaped body's aperture.

19 Claims, 7 Drawing Sheets

ECG ELECTRODE CONNECTOR

FIELD OF THE INVENTION

The present invention relates to a connector, especially to an ECG (electrocardiograph) snap type connector for bioelectric signal sensing devices.

DESCRIPTION OF THE PRIOR ART

There are numerous examples of connectors for use with standard medical snap electrodes. Shortcomings in the prior art when compared to the present invention include large connector diameters or overall dimensions, multiplicity of requisite component parts, the need for intervening wires, and structures without insertion and retention angled contact apertures to support optimizing low insertion force and high retention force characteristics.

Kim discloses in U.S. Pat. No. 8,123,576 issued Feb. 28, 2012 an electrical connector fastened to the end of an electric wire to easily attach or detach a snap electrode to the wire. The present invention differs in that it provides a connection between a snap electrode and an electronic apparatus without an intervening wire.

A snap connector disclosed by Archer in U.S. Pat. No. 4,671,591 issued on Jun. 9, 1987, uses two separate springs to make contact between an electrical wire and a pin electrode. The first spring makes contact with the proximal end of the pin, while the second spring makes contact with a detent distal portion of the pin. This differs from the present invention since the prior art uses a U shaped spring that grips the pin from the side, and also a second clip shaped spring that grips the detent portion of the pin from the side. The present invention also differs in that it provides a connection between a snap electrode and an electronic apparatus without an intervening wire.

U.S. Pat. No. 5,232,383 issued to R. Barnick on Aug. 3, 1993 discloses a medical snap electrode connector to provide an electrical connection between a snap electrode and an electrical wire. The structure uses several flexible contact fingers around the snap electrode contact pin to provide an electrical connection and mechanical retention when the connector is fully engaged. The present invention differs from this prior art in that it uses two opposing resilient contact arms rather than a plurality of flexible contact fingers, and it does not provide a connection for an electrical wire.

Schwarz discloses in U.S. Pat. No. 7,081,026 issued on Jul. 25, 2006, an electrical device for connecting an electrical wire to a medical electrode. Disclosed is a U shaped electrode having two arms with resilient properties to make contact with a pin electrode. Additional moving structures are used to release the pin from the connector. This differs from the present invention in that the U shaped contact does not result in a reduced insertion force (to facilitate connection ease), and a larger retention force (to prevent accidental disconnection). Furthermore, the present invention does not require additional moving structures to provide the desired functionality.

Schwarz discloses in U.S. Pat. No. 6,780,065 issued on Aug. 24, 2004 a device for electrical connection of an electrical lead to a medical skin electrode. The apparatus uses a cored flat plate similar to that disclosed in previously mentioned U.S. Pat. No. 7,081,026, but with a second spring-like extension to the flat plate that can be manually flexed to release the snap electrode pin from the U shaped, cored body. The present invention does not require the complexity of a second structure to help release the connector. Instead the present invention uses a novel assembly to create a larger pin retention force than the force needed to insert the snap electrode pin into the connector assembly.

U.S. Pat. No. 4,842,557 issued Jun. 27, 1989 to Muz discloses a contact device for making an electrically conductive connection to a snap electrode pin by using a cored flat plate with vertical fins, wherein the snap electrode pin is inserted through the cored hole and is retained by the spring-like vertical fins on one side of the flat plate. The present invention does not rely on a cored plate. Furthermore, the vertical arms of the present invention are designed to allow the snap electrode pin to have a lower insertion force and a higher retention force.

U.S. Pat. No. 5,454,739 issued on Oct. 3, 1995 to J. E. Strand discloses an electrical connector between an electrical wire and a biomedical electrode that uses a pivoting structure with fixed jaws and a separate spring that presets the jaws towards a closed position. This arrangement can achieve a high release force and a lower actuation force to make the connection. This differs from the present invention in that it is not used for a snap electrode, it is not compact, and it provides an electrical connection between a biomedical electrode sheet and an electrical wire.

Henderson et al. disclose a snap electrode connector in U.S. Pat. No. 6,487,430 issued on Nov. 26, 2002, that uses two cored flat plates that can slide over each other. The cored holes are slightly larger than the diameter of a snap electrode pin. The connection is achieved by squeezing a structure to slide the flat plates over each other and align the two cored holes with the snap electrode pin. The pin is then inserted through the holes and the squeezed structure is released, locking the two flat plates onto the snap electrode pin. The retention force is greater than the insertion force by selecting the force needed to slide the two plates into alignment. This differs from the present invention in that it provides connection between an electrical wire and a snap electrode, and it does not use a U shaped, spring-like structure to provide electrical and mechanical connection.

Kaminski discloses in U.S. Pat. No. 10,010,259 issued on Jul. 3, 2018, a circuit for a bioelectric signal device wherein an example embodiment illustrates a common medical snap electrode connector. The connector is a self-contained metallic button with an internal C shaped wire spring that communicates with the button housing and inward extending sections of the C shaped wire spring that communicates with a snap electrode. This differs from the present invention in that it is not radially compact and it does not provide angled contact surfaces.

Burnes et al. disclose in U.S. Pat. No. 7,445,522 issued on Nov. 4, 2008, an electrode connector to provide an electrical connection between an electrical wire and a biomedical snap electrode by using a keyhole slotted mating body that is slid sideways to lock the connector to the snap electrode pin. The present invention differs from this by relying on a U shaped body with spring properties to retain the snap electrode pin.

A related application is the use of a U shaped body for connecting to the edge of a printed circuit board. For example, Collier et al. disclose in U.S. Pat. No. 5,037,315 issued on Aug. 6, 1991, an electrical edge connector and a printed circuit board where a U shaped spring-like electrical connection body retains an inserted electrical pin having an enlarged portion, once the enlarged portion is inserted past a shaped position of the electrical connection body. This differs from the present invention in that the insertion and retention forces do not differ in magnitude, and the disclosed prior art does not have utility with a snap electrode.

Additional prior art has disclosed the use of resilient arms or tines to make contact with a pin or plug for audio connector applications. For example, Yu discloses in U.S. Pat. No. 7,833,032 issued on Nov. 16, 2010, an audio connector that uses a plurality of resilient tines to make contact with an inserted plug at several electrically isolated locations along the length of the plug, and with an improved mechanical arrangement that reduces the required flex of the tines so that inelastic deformation of the tines is reduced. Also, an audio connector is disclosed in U.S. Pat. No. 7,108,529 issued on Sep. 19, 2006 to Huang. Several resilient tines make contact at several electrically isolated locations on an audio plug. As a tine is deflected by the insertion of the plug, the motion results in the making and or breaking of one or more electrical contacts between fixed tines and resilient tines. These two prior art inventions differ from the present invention in that they are used for making electrically isolated connections with a plurality of contact points on the plug; they are not useful for snap electrodes; and they do not create a lower plug insertion force and a higher plug retention force.

To overcome the shortcomings, the present invention provides an improved ECG electrode connector to mitigate or obviate the aforementioned problems.

SUMMARY OF THE INVENTION

The main objective of the present invention is to provide an ECG electrode snap type connector that is compact, relatively simple, and readily adapted for printed circuit board (PCB) attachment, while providing good performance for electrical and mechanical mating, low insertion force, and high retention force. The electrical connection and the mechanical retention of the connector function is provided by a channeled U shaped body that is able to be stamp cut and bent to shape from a single thin sheet of electrically conductive and resilient material. The channeled U shaped body is formed to communicate with a fixed structure that can be added in order to limit the deflection range of resiliency and can be made very small. The inner portion of the channeled U shaped body is formed to communicate with the snap portion of an ECG snap type electrode. Whereby, the present invention provides a compact PCB mountable connecting structure that is easy to manufacture and easy to configure for low insertion force and high retention force, with good electrical and mechanical connection.

Other objectives, advantages and novel features of the invention will become more apparent from the following detailed description when taken in conjunction with the accompanying drawings.

DETAILED DESCRIPTION OF THE INVENTION

The invention disclosed herein refers to embodiments and process for creating embodiments of ECG electrode snap type connector that is compact, relatively simple to fabricate, and readily adapted for printed circuit board (PCB) attachment, while providing good performance for electrical and mechanical mating, low insertion force, and high retention force.

Figure 1:
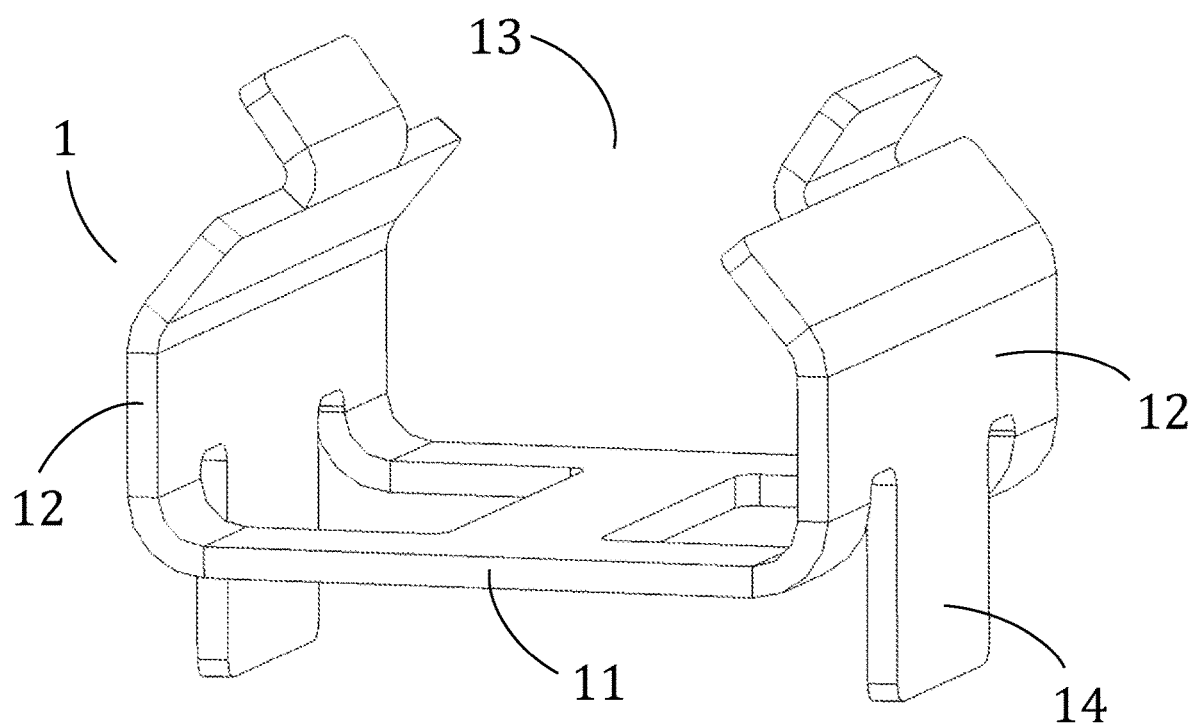
FIG. 1 is a perspective view of a connector electrical and mechanical contacting body in accordance with the present invention.
Figure 2:
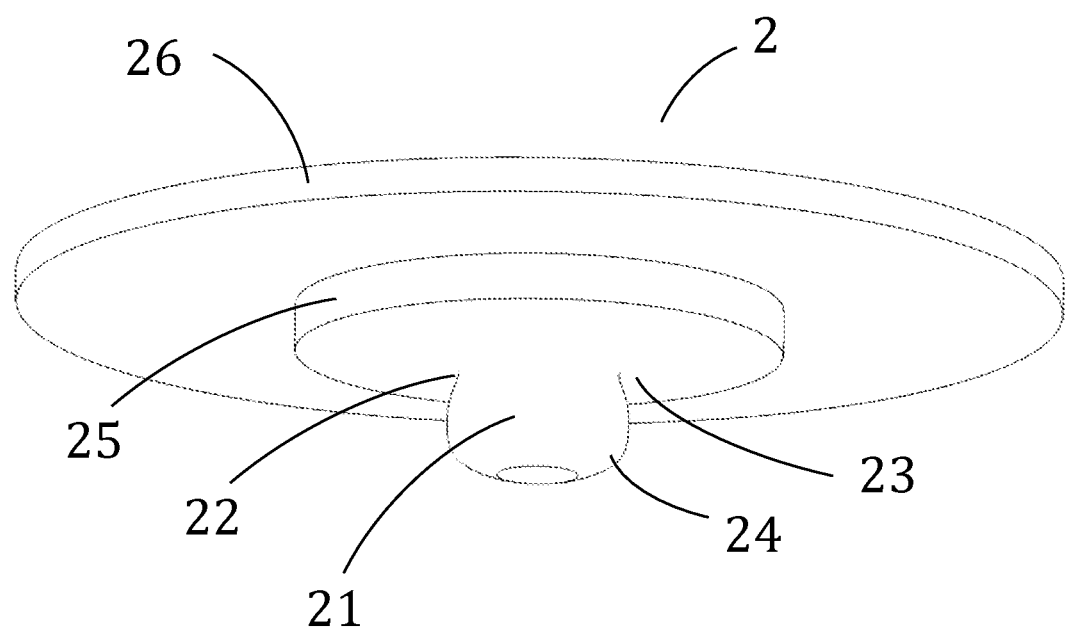
FIG. 2 is a perspective view of a common ECG snap type electrode.

With reference to FIGS. 1 and 2, a preferred embodiment of the present invention comprises a compact channeled U shaped body (1) for connecting common ECG snap type electrodes (2) to bioelectric signal sensing devices, where compact channeled U shaped body (1) comprises a U base (11), two U side arms (12), a U aperture (13), and preferably PCB mounting tabs (14) or other PCB attachment means.

Common ECG snap type electrodes (2) comprise ECG electrode skin pad (26) which is typically coated with an adhesive biocompatible electrolyte and snap pin connector body (25) that provides electrical and mechanical connection means.

Figure 3:
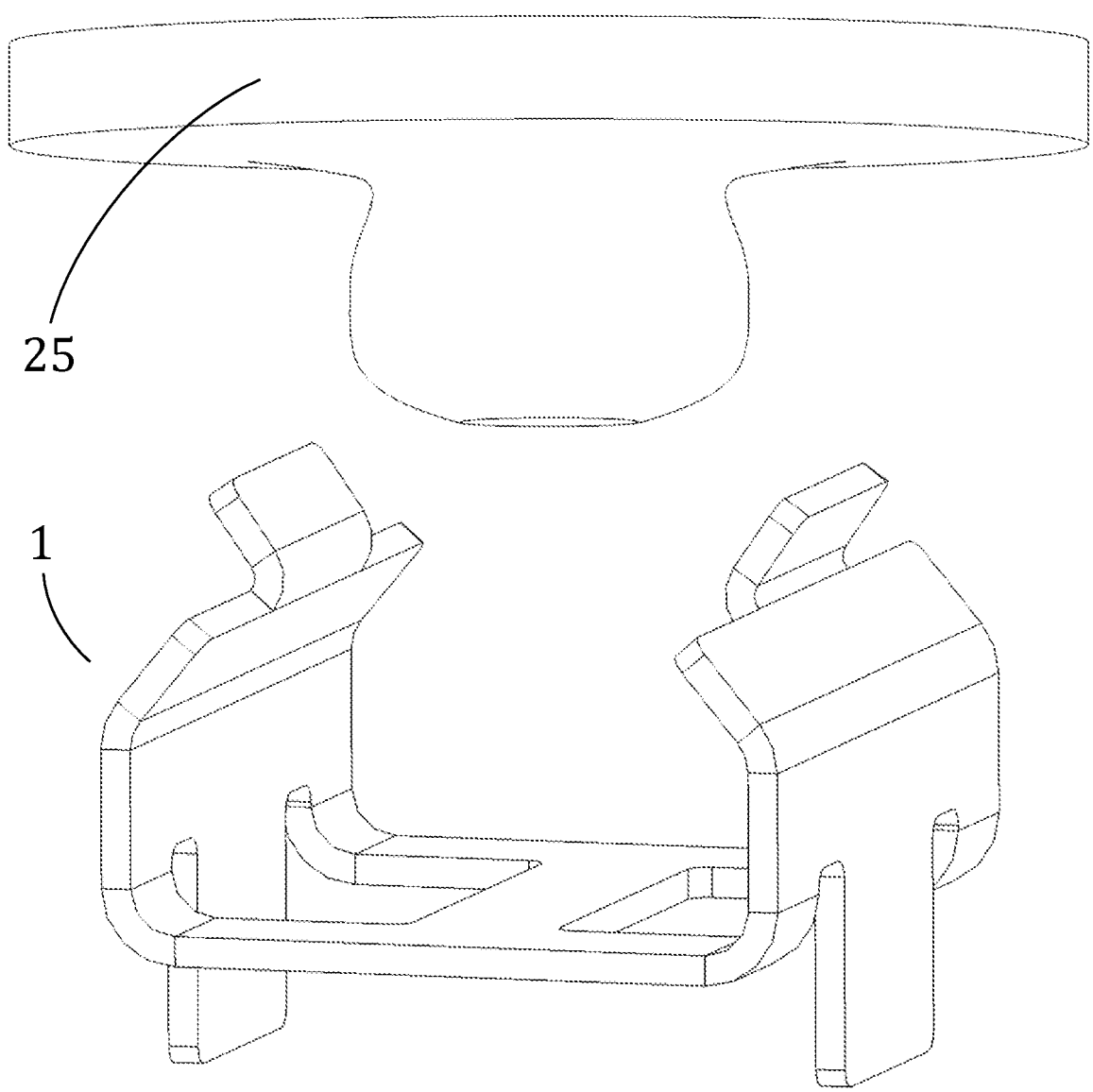
FIG. 3 is a perspective view of a common ECG snap type electrode connector base shown in alignment for mating with the connector body of FIG. 1.
Figure 4:
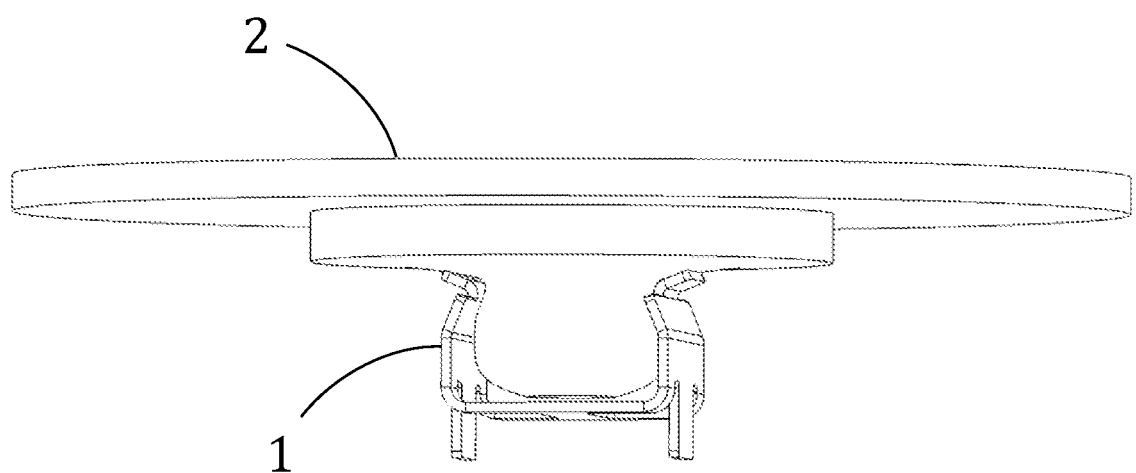
FIG. 4 is a perspective view of the electrode of FIG. 2 seated in the connector body of FIG. 1.

With further reference to FIGS. 3 and 4, snap pin body (25) is inserted for mating with channeled U shaped body (1) oriented along their respective axes of symmetry whereupon mating is achieved with ECG electrode (2) seated and retained by channeled U shaped body (1) with snap pin shoulder (23) in proximity to the distal ends of U side arms (12) and snap pin head crown (24) in proximity to U base (11).

The U aperture (13) is shaped to receive a snap pin head (21) into the channeled U shaped body (1). The distal ends of U side arms (12) are angled to communicate with snap pin head crown (24) in order to provide spreading of the U aperture (13) for insertion and to communicate with snap pin neck (22) when mated in order to provide electrical contact with snap pin body (25) at two points of contact as well as mechanical retention force provided primarily or partly by the flat spring bend characteristics of said resilient U side arms (12). The inner region of U aperture (13) is relieved to accommodate snap pin head (21) in order that said communication of U side arms (12) with snap pin neck (22) is not impinged and with said relief angled to provide spreading of U aperture (13) for extraction. The aforementioned angles for spreading the channeled U shaped body (1) when in communication with a snap pin head (21) provides means by which the present invention features the ability to further design optimize the tradeoff between insertion force and retention force.

Figure 5:
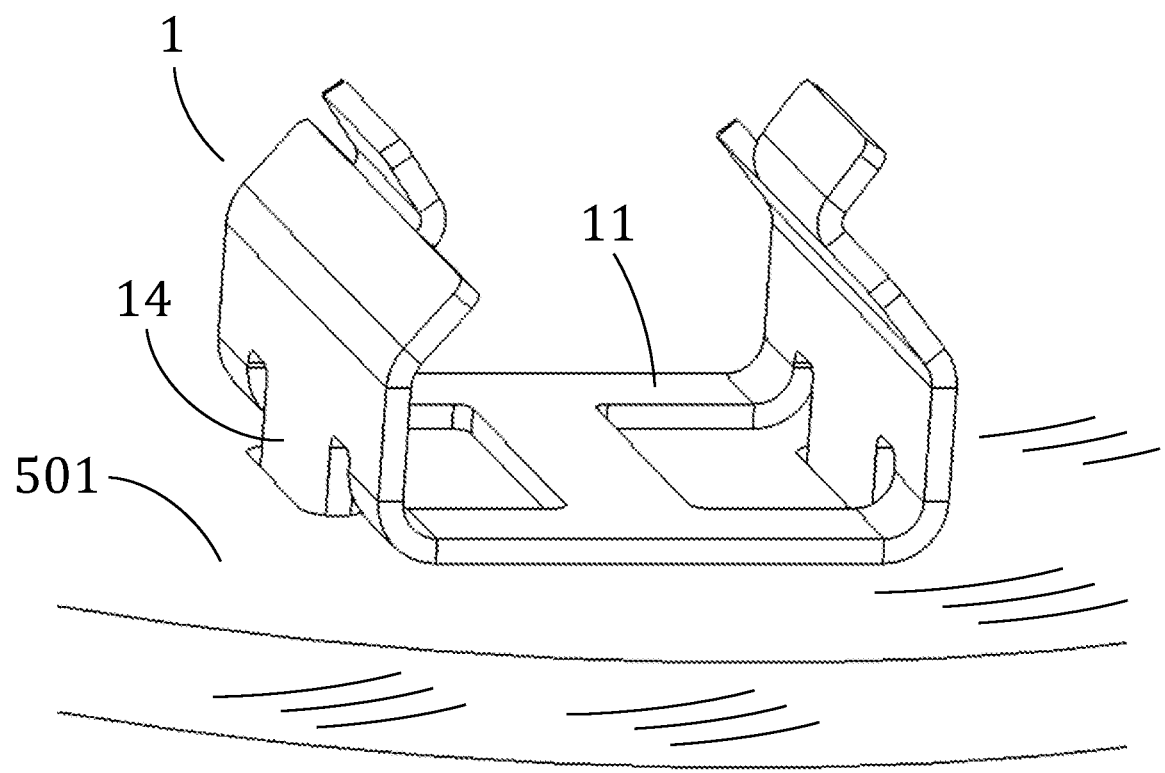
FIG. 5 is a perspective view of the connector body of FIG. 1 shown mounted to a printed circuit board.
Figure 6:
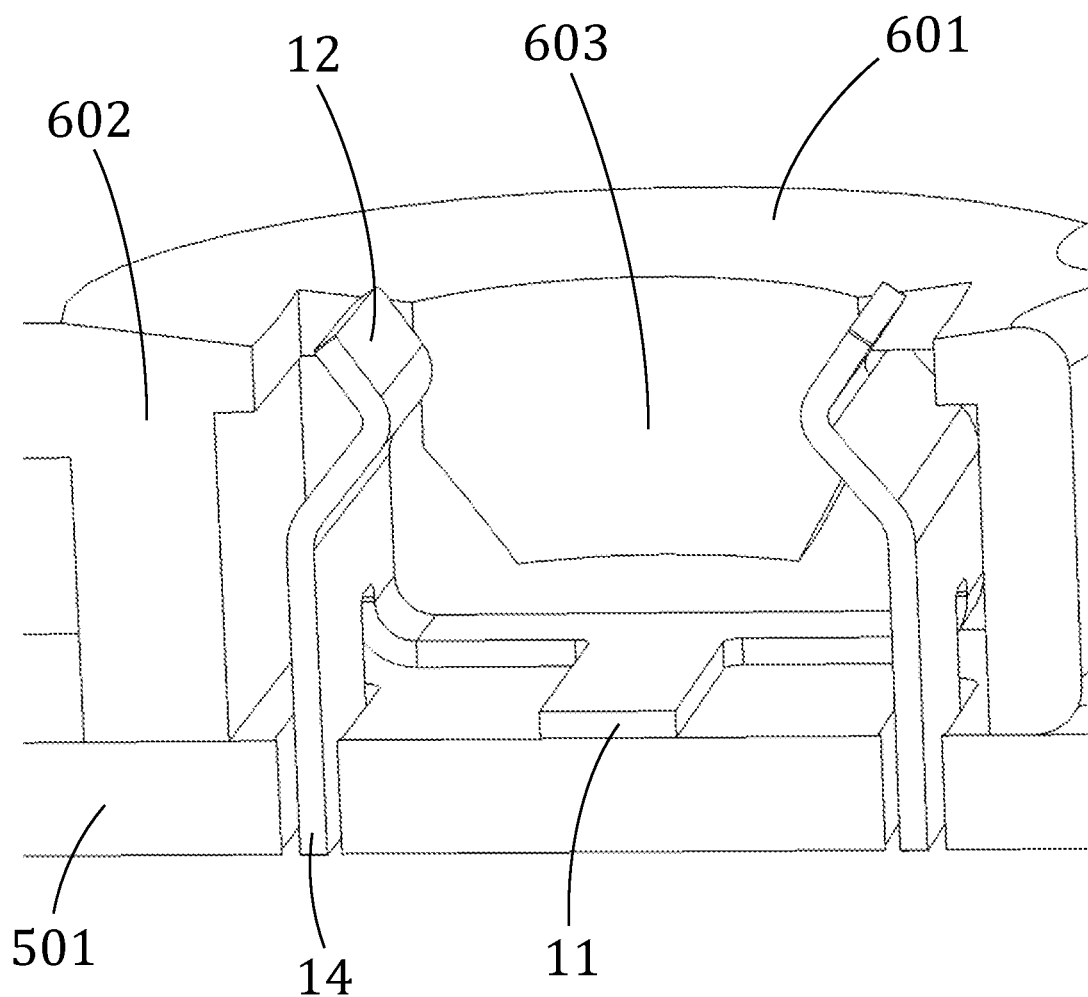
FIG. 6 is an operational perspective view in partial section of the connector body of FIG. 1 shown housed in fixed structures which limit expansion and contraction.

With further reference to FIGS. 5 and 6, another preferred embodiment comprises channeled U shaped body (1) attached to PCB (501) with U base (11) in communication with the surface of PCB (501). A preferred embodiment comprises PCB through-hole mounting tabs (14) providing means for attachment to PCB (501). Although herein described are PCB through-hole mounting tabs, further adaptations of the present invention may comprise pins or surface-mount PCB pads.

With particular reference to FIG. 6, additional preferred embodiment comprises fixed structure (601) made of rigid and preferably electrically isolating material such as plastic, more preferably acrylonitrile butadiene styrene (ABS), high density polyethylene, nylon, acrylic, polypropylene, polystyrene, polycarbonate, or polyethylene terephthalate, in proximity to U side arms (12) such that expansion of the U side arms (12) is limited upon communication with expansion limiting structure (602). More preferably, said expansion is limits the expansion of the narrowest U aperture (13) section to maximum dimension in the range of 3 mm to 6 mm.

Another preferred embodiment comprises closure limiting structure (603) that limits the amount of closure of U aperture (13) from resiliency or other forces applied to U side arms (12) upon physical contact of U side arms (12) with closure limiting structure (603), which in turn provides: (a) fixed and advantageous dimensioning for the ECG connector receptacle, and (b) advantageous spring constant values for the base material of channeled U shaped body (1) provided by pre-tensioning of the flat spring bend of U side arms (12). More preferably, said U aperture (13) contraction limit has a minimum dimension in the range of 1 mm to 4 mm.

Figure 7:
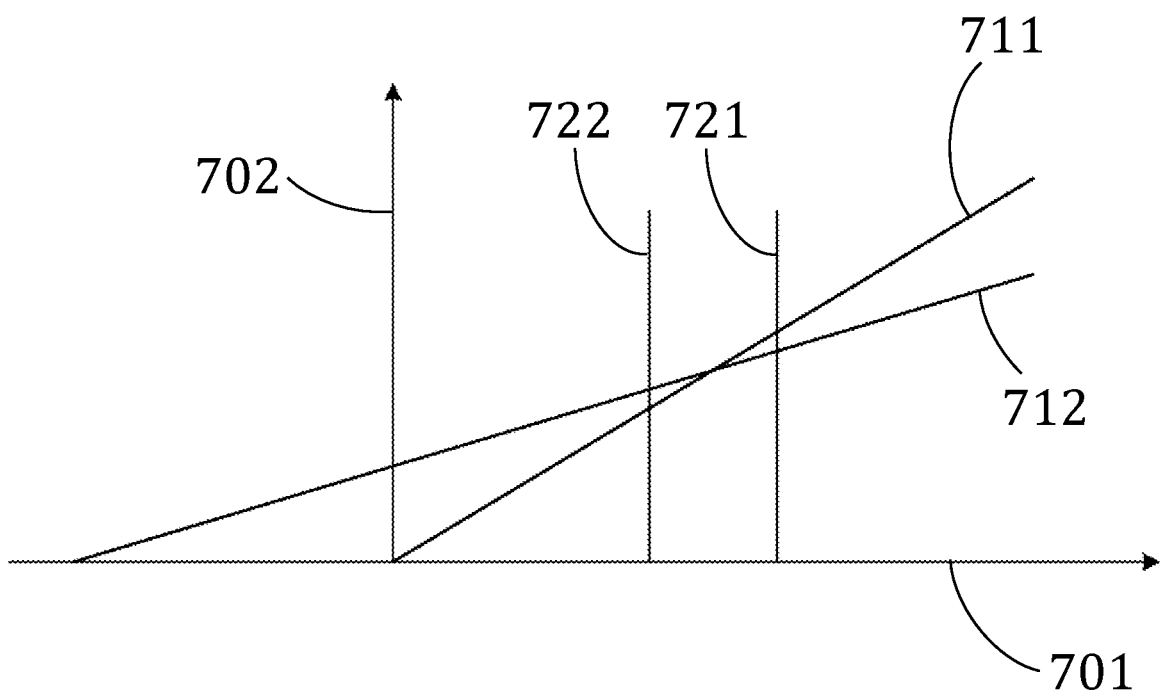
FIG. 7 is a graph showing the effect of pre-tensioning the connector body of FIG. 1 with the fixed structures of FIG. 6.

With further reference to FIG. 7, advantages of the aforementioned pre-tensioning are a low insertion force and a high retention force provided by the present invention. The relationship between U side arm displacement (701) and U side arm spring force (702) is determined by the value of the spring constant of the material of the channeled U shaped body (1). Without pre-tensioning, a spring constant (711) is required in order that acceptable forces are presented at the maximum insertion displacement (721) as well as the retention displacement (722). However with pre-tensioning, a lower spring constant (712) is possible which effectively decreases the insertion force while at the same time increases the retention force, both in comparison to the forces presented without pre-tensioning.

Another preferred embodiment of the present invention comprises fixed structure (601) formed as part of a housing that encapsulates the PCB (501).

Another preferred embodiment of the present invention comprises the compact channeled U shaped body (1) die cut and bent from a single thin sheet of electrically conductive and resilient material. With reference to FIG. 1, cuts in the U base (11) provide for the extension of the PCB through-hole mounting tabs (14) in 180 degree opposition to the bend at the proximal end of the U side arms (12), while achievable with a single bend operation.

Further advantages of the present invention are provided by a preferred embodiment comprising two points of contact between channeled U shaped body (1) and snap pin head (21), wherein two points of contact, in comparison to one point of contact, provides improvements in electrical connection characteristics and spring force optimization; the prior provided by doubling the contact surface area, and the latter provided by doubling the spring displacement.

A preferred embodiment of the present invention comprises channeled U shaped body (1) made of a metal material which is readily tempered for spring characteristics, more preferably selected from the list of phosphor bronze, beryllium copper or spring nickel; and coated or plated with a thin layer of metal or metals, more preferably selected from the list of gold, silver, platinum, nickel, tin, zinc, chromium, rhodium, or combinations of these.

Further preferred embodiments of the present invention comprises channeled U shaped body formed from a thin sheet that has a thickness in the range of 0.05 mm to 0.5 mm, a channel length in the range of 1 mm to 10 mm, U side arms with a height in the range of 1 mm to 10 mm, U base with a length in the range of 1 mm to 10 mm, and U aperture with a span in the range of 1 mm to 5 mm.

Even though numerous characteristics and advantages of the present invention have been set forth in the foregoing description, together with details of the structure and features of the invention, the disclosure is illustrative only. Changes may be made in the details, especially in matters of shape, size, materials, and arrangement of parts within the principles of the invention to the full extent indicated by the broad general meaning of the terms in the appended claims as expressed.

What is claimed is:

1. A compact structure for connecting common ECG snap type electrodes to bioelectric signal sensing devices, with said structure comprising a channeled U shaped body formed from one or more thin sheets of electrically conductive and resilient material, with a U base and two U side arms creating a U aperture;
   where said common ECG snap type electrode comprises snap pin head, snap pin neck, snap pin shoulder, and snap pin head crown;
   where the snap pin is mated to the channeled U shape body with their respective axes of symmetry aligned and the snap pin being inserted from the opening at the top of the U shape until the snap pin head crown is in proximity to the U base, and where U side arms are shaped with angles forming an indented narrowed aperture portion in proximity to the fully inserted snap pin neck where mating contact is provided;
   with resiliency of the U aperture at or near the open ends of the U side arms provided primarily or partly by the flat spring bend characteristics of said resilient U side arms;
   with the angle of narrowing between the top of the U shape and the indented narrowed aperture portion of U side arms being chosen for a desired insertion force and the angle of narrowing between the U side arm midsection and the narrowed aperture portion being chosen for a desired retention force;
   with electrical and mechanical connection means for attachment to a bioelectric signal sensing device printed circuit board (PCB) located at or near the U base;
   with additional fixed structure providing a mechanical limit to the extent of U aperture expansion;
   and with additional fixed structure providing a mechanical limit to the extent of U aperture closure.

2. The compact structure of claim 1 where the channeled U shaped body is comprised of a metal material which is readily tempered for spring characteristics, more preferably selected from the list of phosphor bronze, beryllium copper or spring nickel.

3. The compact structure of claim 1 where the channeled U shaped body is plated or coated with a thin layer of metal or metals, more preferably selected from the list of gold, silver, platinum, nickel, tin, zinc, chromium, rhodium, or combinations of these.

4. The compact structure of claim 1 where the fixed structures providing mechanical limit of the extent of U aperture closure and expansion are comprised of a rigid electrically insulating material such as plastic, more preferably acrylonitrile butadiene styrene (ABS), high density polyethylene, nylon, acrylic, polypropylene, polystyrene, polycarbonate, or polyethylene terephthalate.

5. The compact structure of claim 1 where electrical and mechanical connection to a bioelectric signal sensing device printed circuit board located at or near the U base is selected from the list of provided by surface mount pads or though-hole mounting tabs or pins.

6. The compact structure of claim 1 where electrically conductive and resilient material is used to from the channeled U shaped body with sheet metal bends forming U arms extension above the U base while simultaneously forming through-hole PCB mounting tabs extension below the U base.

7. The compact structure of claim 1 where the channeled U shaped body is formed from a thin sheet that has a thickness in the range of 0.05 mm to 0.5 mm.

8. The compact structure of claim 1 where the channeled U shaped body has a channel length in the range of 1 mm to 10 mm.

9. The compact structure of claim 1 where each U side arm has a height in the range of 1 mm to 10 mm.

10. The compact structure of claim 1 where the U base has a length in the range of 1 mm to 10 mm.

11. The compact structure of claim 1 where the U aperture has a span in the range of 1 mm to 5 mm.

12. The compact structure of claim 1 where the fixed structures providing mechanical limit of the extent of U aperture closure and expansion are formed as part of a housing that encases the printed circuit board.

13. The compact structure of claim 1 where the fixed structures providing mechanical limit of the extent of U aperture closure and expansion are configured to limit the expansion of the narrowest U aperture section to maximum dimension in the range of 3 mm to 6 mm.

14. The compact structure of claim 1 where the fixed structures providing mechanical limit of the extent of U aperture closure and expansion are configured to limit the contraction of the U aperture to minimum dimension in the range of 1 mm to 4 mm.

15. A process for creating a compact structure for connecting common ECG snap type electrodes to bioelectric signal sensing devices, comprising:

forming a channeled U shaped body from one or more thin sheets of electrically conductive and resilient material, with a U base and two U side arms creating a U aperture;

designing the channeled U shaped body to mate with the snap pin with their respective axes of symmetry aligned and the snap pin being inserted from the opening at the top of the U shape until the snap pin head crown is in proximity to the U base, and shaping U side arms with angles forming an indented narrowed aperture portion in proximity to the fully inserted snap pin neck where mating contact is provided;

incorporating resiliency into the U aperture at or near the open ends of the U side arms primarily or partly by selecting the flat spring bend characteristics of said resilient U side arms;

designing a U aperture with the angle of narrowing between the top of the U shape and the indented narrowed aperture portion of U side arms being chosen for a desired insertion force and the angle of narrowing between the U side arm midsection and the narrowed aperture portion being chosen for a desired retention force;

incorporating an electrical and mechanical connection means for attachment to a bioelectric signal sensing device printed circuit board located at or near the U base;

designing additional fixed structure to provide a mechanical limit the extent of U aperture expansion;

and designing additional fixed structure to provide a mechanical limit to the extent of U aperture closure.

16. The process of claim 15 where the channeled U shaped body is made of a metal material which is readily tempered for spring characteristics, more preferably selected from the list of phosphor bronze, beryllium copper or spring nickel.

17. The process of claim 15 where the channeled U shaped body is plated or coated with a thin layer of metal or metals, more preferably selected from the list of gold, silver, platinum, nickel, tin, zinc, chromium, rhodium, or combinations of these.

18. The process of claim 15 where the fixed structures providing mechanical limit of the extent of U aperture closure and expansion are made of a rigid electrically insulating material such as plastic, more preferably acrylonitrile butadiene styrene (ABS), high density polyethylene, nylon, acrylic, polypropylene, polystyrene, polycarbonate, or polyethylene terephthalate.

19. The process of claim 15 where electrically conductive and resilient material is used to from the channeled U shaped body with sheet metal bends forming U arms extension above the U base while simultaneously forming through-hole PCB mounting tabs extension below the U base.

* * * * *